US006348213B1

(12) United States Patent
Barenholz et al.

(10) Patent No.: US 6,348,213 B1
(45) Date of Patent: Feb. 19, 2002

(54) METHOD FOR REVERSING AGE-RELATED CHANGES IN HEART MUSCLE CELLS

(75) Inventors: Yechezkel Barenholz, Jerusalem (IL); Elishalom Yechiel, Baltimore, MD (US)

(73) Assignees: Yissum Research and Development Co. of The Hebrew University of Jerusalem; Hadassah Medical Organization, both of (IL)

( * ) Notice: Subject to any disclaimer, the term of this patent is extended or adjusted under 35 U.S.C. 154(b) by 0 days.

(21) Appl. No.: 08/238,149

(22) Filed: May 3, 1994

Related U.S. Application Data

(63) Continuation of application No. 07/986,664, filed on Jan. 22, 1993, now abandoned, which is a continuation of application No. 07/714,069, filed on Jun. 12, 1991, now abandoned, which is a continuation of application No. 07/323,516, filed on Mar. 14, 1989, now abandoned, which is a continuation of application No. 06/832,929, filed on Feb. 24, 1986, now Pat. No. 4,737,323.

(51) Int. Cl.[7] .................. A61K 9/127; A61K 9/133; A61K 31/685
(52) U.S. Cl. .................. 424/450; 128/DIG. 3; 428/402.2; 436/829; 514/78; 514/824; 514/878; 514/879
(58) Field of Search .................. 428/402.2; 514/78, 514/824, 878, 879; 436/829; 128/DIG. 3; 424/450

(56) References Cited

U.S. PATENT DOCUMENTS

| | | | | |
|---|---|---|---|---|
| 4,308,166 A | * | 12/1981 | Marchetti et al. | 424/450 |
| 4,310,505 A | * | 1/1982 | Baldeschwieler et al. | 428/402.2 X |
| 4,544,545 A | * | 10/1985 | Ryan et al. | 424/450 |
| 4,812,314 A | * | 3/1989 | Barenholz et al. | 424/450 |

FOREIGN PATENT DOCUMENTS

| | | | |
|---|---|---|---|
| GB | 2089681 | * | 6/1982 |

OTHER PUBLICATIONS

Walter W. Stafford and Charles E. Day The Upjohn Company, Kalamazoo, Michigan 49001 ARTERY 1(2):106–114 (1975), pp. 106–114..

A.N. Howard, J. Patelski, D. Bowyer & A. Gresham Atherosclerosis Induced in Hypercholesterolaemic Baboons by Immunological Injury: and the Effects of Intravenous Polyunsaturated Phosphatidyl Choline. Atherosclerosis 1971 14:17–29.

J. Patelski, D. Bowyer, A. Howard, I. Jennings, C. Thorne & G. Gresham. Modification of Enzyme Activities in Experimental Atherosclerosis in the Rabbit. Atherosclerosis, 1970, 12: 41–53.

Meyer Friedman, Sanford O. Byers, and Ray H. Rosenman Resolution of Aortic Atherosclerotic Infiltration in the Rabbit by Phosphatide Infusion (23300) Lecithin (Animal) 90% Pure, purchased from Nutritional Biochemicals Corp. Cleveland, O. pp. 586–588.

Barenholz, Y., et al, Biochem Biophys Acta, 604:129 (1980).

Barenholz, Y., et al, in Phospholipids (Hawthorne, J.N., et al, eds.).

Barenholz, Y., in Physiology of Membrane Fluidity (Shinitsky, M., ed.) vol:131–173, CRC Press, Boca Raton, FL (1984).

Cooper, R.A., et al, New England J Med, 297:371 (1977).

Frank, A., et al, Biochem, 22:5647 (1983).

Martin, F.J., et al, Biochem, 15:321 (1976).

Pagano, R.E., et al, inResearch Monographs inCell and Tissue Physiology (Dingle, J.T., et al, eds.), vol. 7, pp 323–348 (1982).

Yechiel, E., et al, J Biol Chem, 260(16):9123 (1985a).

Yechiel, E., et al, JBiol Chem, 260(16):9131 (1985b).

Kevin Jon Williams, Victoria P. Werth and John A. Wolff Intravenously Administered Lecithin Liposomes: A Synthetic Antiatherogenic Lipid Particle. Perspectives in Biology & Medicine, 27, 3 Spring 1984/417 thru p. 431.

Sanford O. Byers and Meyer Friedman. Transport of Cholesterol During Phosphatide–Induced Hypercholesterolemia. Biochim. Biophys. Acta, 125 (1966) 157–165.

Sanford O. Byers, Meyer Friedman and Toshiko Sugiyama Mechanism Underlying Phosphatide–Induced Hypercholesterolemia The Journal of Biological Chemistry vol. 237, No. 11 Nov. 1962 Printed in U.S.A.

Barenholz, Y., et al, Biochemistry, 15:2441 (1976a).

Barenholz, Y., et al, in Enzymes in Lipid Metabolism (Gatt, S., et al, eds.), pp 45–56. Plenum Press, NY (1976b).

Barenholz, Y., et al, Biochemistry, 16:2806 (1977).

Barenholz, Y., et al, in Phospholipids (Hawthorne, J.N., et al, (eds.). (1982).

* cited by examiner

Primary Examiner—Richard D. Lovering
(74) Attorney, Agent, or Firm—Foley & Lardner

(57) ABSTRACT

A method of-treating a relatively aged animal to reverse age-related changes in the lipid composition of organ and tissue cells, such as heart muscle cells, and the ability of the animal to withstand respiratory stress. A suspension of small unilamellar vesicles composed predominantly of egg phosphatidyl choline is administered parenterally to the animal, preferably over a period of several days and at a dose level of between about 0.1 and 1 grams lipid per kg body weight per day. Changes in the heart muscle cells are reflected in decreased levels of serum creatine phosphokinase. Liposome administration is continued until the serum creatine phosphokinase level drops at least about 50%. Also disclosed are liposome treatment methods for increasing longevity and male fertility.

3 Claims, No Drawings

METHOD FOR REVERSING AGE-RELATED CHANGES IN HEART MUSCLE CELLS

This application is a continuation of application Ser. No. 07/986,664 filed on Jan. 22, 1993 (now abandoned), which is a continuation of application Ser. No. 07/714,069 filed on Jun. 12, 1991 (now abandoned), which is a continuation of application Ser. No. 07/323,516 filed on Mar. 14, 1989 (now abandoned), which is a continuation of application Ser. No. 06/832,929 filed on Feb. 24, 1986, (and now U.S. Pat. No. 4,737,323 issued on Mar. 14, 1989)

BACKGROUND OF THE INVENTION

The present invention relates to a method for reversing age-related changes in the lipid composition of heart muscle tissue and other age-related physiological characteristics.

REFERENCES

1. Barenholz, Y., et al, Biochemistry, 15:2441 (1976a).
2. Barenholz, Y., et al, in Enzymes in Lipid Metabolism (Gatt. S., et al, eds.), pp 45–56, Plenum Press, NY (1976b).
3. Barenholz, Y., et al, Biochemistry, 16:2806 (1977).
4. Barenholz, Y., et al, Biochem Biophys Acta, 604:129 (1980).
5. Barenholz, Y., et al, in Phospholipids (Hawthorne, J. N., et al, eds.).
6. Barenholz. Y., in Physiology of Membrane Fluidity (Shinitsky, M., ed.) Vol:131–173, CRC Press, Boca Raton, Fla. (1984).
7. Bartlett, G. R., J Biol Chem, 234:466 (1959)
8. Borochov, H., et al, Biochem, 18:251 (1979).
9. Cooper, R. A., et al, New England J Med. 297:371 (1977).
10. Cooper, R. A. et al, Biochem, 17:327 (1978).
11. Folch, J., et al, J Biol Chem, 226:497 (1957).
12. Frank, A., et al, Biochem, 22:5647 (1983).
13. Harary, I., et al, Exper Cell Res, 29:451 (1963).
14. Hasin, Y., J Mol Cell Cardiol, 12:675 (1980).
15. Hertz, R., et al, Chem Phys Lipid, 15:138 (1975).
16. Jourdon, P., et al, J Mol Cell Cardiol, 12.1441 (1980).
17. Kader, J.-C., et al, in New Comprehensive Biochemistry (Neuberger, A., et al, eds.), Vol 4: 279–311, Elsevier Biomedical Press (1982).
18. Levida, M., Handbook of Nutrition in the Aged (R. R. Watson, ed.), CRC Press, pp. 89–109 (1985).
19. Martin. F. J., et al, Biochem, 15:321 (1976).
20. Pagano, R. E., et al, in Research Monographs in Cell and Tissue Physiology (Dingle, J. T., et al, eds.), Vol 7, pp 323–348, Elsevier/North Holland (1982).
21. Pal, R., et al, J Biol Chem, 255(12):5802 (1080).
22. Richards, g. M., Anal Biochem, 57:369 (1974).
23. Shinitsky, M., et al, J Biol Chem, 249:2652 (1974).
24. Szoka, F., et al, Ann Rev Biophys Bioeng, 9:467 (1980).
25. Wallach, D. F. N., in Membrane Biology of Neoplastic Cells, Elsevier, Amsterdam (1975).
26. Wirtz, K. W. A., et al, J Biol Chem, 243:3596 (1968).
27. Yavin, E., et al, Anal Biochem, 80:530 (1977).
28. Yechiel, E., et al, J Biol Chem, 260(16):9123 (1985a).
29. Yechiel, E., et al, J Biol Chem, 260(16):9131 (1985b).

BACKGROUND OF THE INVENTION

One of the biochemical changes which occur with aging is a change in membrane lipid composition. In mammalian plasma membranes, the main variation occurs in the relative composition of phosphatidylcholine (PC). which decreases with age, and sphingomyelin (SM) and cholesterol, which increase with age (Barenholz). The changes in the relative amounts of PC and SM is especially great in tissues which have a low phospholipid turnover. For example, plasma membranes associated with the aorta and arterial wall show a 6-fold decrease in PC/SM ratio with aging. SM also increases in several diseases, including atherosclerosis. The SM content can be as high as 70–80% of the total phospholipids in advanced aortic lesion (Barenholz 1982, 1984).

The most striking differences between PC and SM derived from biological membranes are (a) the phase transition temperature of the lipids, and (b) the hydrogen-bonding character of the two lipids in a lipid-bilayer. Most sphingomyelins have transition temperatures in the physiological temperature range between 30° and 40° C., whereas most naturally occurring phosphatidylcholines are well above their transition temperature at 37° C. (Barenholz 1980, 1982, 1984). In terms of hydrogen bonding, the difference in the polar regions of these two lipids enables SM to be both a donor and acceptor of hydrogen in hydrogen bonding, while PC can only serve as a hydrogen donor.

Whether or not related to these differences, the relative content of PC to SM in mammalian plasma membranes appears to affect cell functioning significantly. The inventors and colleagues have recently reported on changes in the lipid composition and activity of primary rat myocytes in culture over time. Measurements of PC and SM content in the cells showed a decline of PC/SM ratio from 5 to about 2 in the first three days in culture, and from 2 to about 1 over the next 14 days in culture. The lipid composition changes were accompanied by a dramatic change in heart cell activity, as measured by the beating rate of the cultured cells. Between days 7 and 12 in culture, the beats/minute fell from about 160 to about 20, and significant increases in the activities of at least seven enzymes, expressed as Vmax/DNA, were also observed. One of these enzymes was creatine phosphokinase (CPK), which plays a major role in intracellular energy transport from mitochondria to myofibrils, and in the regulation of energy production coupled to energy utilization (Yechiel 1985a, 1985b).

The ratio of cholesterol to phospholipid also appears to be an important determinant in regulating the properties of biological membranes (Cooper 1977). Several studies have shown that certain properties of biological membranes can be altered by enrichment with or depletion of cholesterol (Borochov, Cooper 1978, Hasin). In general, there is a strong positive correlation between changes in SM and cholesterol levels in mammalian plasma membranes. That is, changes in the content of one are followed by changes in the other (Wallach, Barenholz 1982, 1984).

It is not clear how cells maintain the various lipid compositions in their different membranes, or why lipid composition changes with aging. In theory, lipid compositional changes could result from changes in the rates of synthesis or degradation of specific lipid components, or changes in the rate of lipid exchange or transfer between serum and the cell membrane. The latter mechanism has received considerable attention with regard to in vitro studies on lipid exchange in cultured biological cells. A number of studies have shown lipid exchange between biological membranes and artificial lipid bilayer vesicles or liposomes (Pagano, Martin, Cooper 1977, Frank). In general, phospholipid exchange between cells and liposomes is accelerated by the presence of a variety of phospholipid transfer proteins, including high and low density serum apolipoproteins (Wirtz, Kader). Cholesterol exchange between biological membranes and liposomes, and/or serum lipoprotein particles is also well known (Hasin, Grunze, Pal).

The ability to alter the lipid composition of biological cells by lipid exchange provides a means for studying the effect of lipid variation on cell function. For example, in the above-discussed myocyte culture system in which a decline in PC/SM ratio over time is accompanied by a drop in beating frequency, it can be asked whether (a) the original lipid composition of the cells can be restored by lipid exchange; and (b) if so, if original cell functioning, i.e., initial beating rate, is also restored. The inventors and coworkers have investigated this question, using small unilamellar PC liposomes as a vehicle for lipid exchange with the cells (Yechiel 1985a, 1985b). The study showed that lipid exchange increased both PC/SM and PC/cholesterol ratios, and thus reversed the normal lipid compositional changes which occur in the cultured cells over time. Interestingly, lipid exchange also restored cell beating frequency to its original levels, with the beating frequency showing a jump from about 20 to 160 within one day of cell exposure to the PC liposomes. Lipid exchange also led to a reduction in cellular enzymes, such as CPK, which were normally increase with time in culture.

SUMMARY OF THE INVENTION

According to an important aspect of the present invention, it has been discovered that PC-rich liposomes are able to reverse age-related changes in the lipid composition of heart muscle cells in animals which have received the liposomes by parenteral administration. One significant benefit of the liposome treatment is that the ability to withstand respiratory stress, which normally shows a gradual loss with increasing age (starting above the age of about 15 months in rats), is significantly improved. Furthermore, lipid exchange and concomitant improvement in respiratory hardiness are produced within several days of initial liposome administration. The method is applicable to both veterinary animals and humans.

According to another aspect of the invention, the effect of liposome treatment on heart muscle lipid exchange is reflected in a number of physiological changes which can be readily observed in serum samples from the treated individual (veterinary animal or human). One of these changes is a decrease in the serum creatine phosphokinase (CPK), to levels which are characteristic of relatively younger animals. Typically, serum CPK in a relatively aged animal will fall by 50% or more several days after liposome administration is first begun. Another change which is readily observable in the treated animal is greater tolerance of the red blood cells to osmotic shock. Again this change is seen most strongly in the older animals, with the cells from the treated individual showing an osmotic fragility which is characteristic of the animal at a younger age. The change in osmotic fragility presumably is due to a greater PC/SM and/or phospholipid/cholesterol ratio which occurs in red blood cells as a result of the liposome treatment.

In practicing the method, there is provided a suspension of liposomes containing substantially more PC and substantially less SM than that characteristically found in heart tissue from individuals of about the same age. In one preferred embodiment, the liposomes are small unilamellar vesicles (SUVs) having sizes predominantly between 0.02 and 0.08 microns, and composed predominantly or exclusively of purified PC such as egg PC. The liposome suspension is administered in an amount which is effective to produce, over a period of at least several days, a substantial decrease in the level of serum CPK in the treated animal. The course of treatment can be followed by monitoring blood CPK or changes in blood cell lipid composition or osmotic fragility.

Another important use of the liposome treatment-method is for increasing longevity in the treated individual. Studies on laboratory animals indicate that treating relatively aged animals with liposomes over an extended period increases animal lifespan by an average of about 36%.

Still another important use of the method is for increasing male sexual competence. Treating relatively old lab animals with liposomes according to the invention reversed the near-complete loss of competence normally seen in the older male animals. The method is particularly useful for treating older breeding animals.

Accordingly, it is a general object of the invention to provide a method of treating an aged individual which significantly enhances the animal's ability to withstand respiratory stress.

A related object of the invention is to provide such a method which reverses age-related lipid composition changes in heart muscle cells.

Another object of the invention is to provide such a method in which the course of treatment can be easily monitored by changes in serum enzyme levels or red blood cell properties.

It is yet another object of the invention is to provide a method which leads to qualitative benefits in aged individuals, including greater longevity and sexual function.

These and other objects and features of the invention will be more fully appreciated from the following detailed description of the invention.

DETAILED DESCRIPTION OF THE INVENTION

1. Preparation of Liposomes

A. Unsized Liposomes

The invention involves, in one aspect, administering liposomes parenterally to an individual (a veterinary animal or human) to reverse age-related changes in the lipid composition of organs and tissues. such as heart muscle cells and red blood cells, by lipid exchange. Since the aging process in heart muscle is characterized in decrease in PC, and a concomitant increase in SM and cholesterol, the liposomes are designed to promote exchange of PC from liposomes to heart cell membrane, and exchange of SM from the heart muscle to the liposomes. The liposomes are also preferably designed to promote cholesterol exchange from the organs and tissues, such as heart muscle cells and red blood cells, to the liposomes.

In order to promote the desired lipid exchange. the mole percent of liposomal PC is substantially greater than, and the mole percent of SM is substantially less than, that of heart tissue from the treated individual, i.e., the PC and SM levels characteristic of individuals of the same age, species, and sex. Preferably the liposomes contain at least about 25 mole percent more PC and at least about 10 mole percent less SM than the heart muscle cells in the treated individual. In one preferred liposome preparation described and used in Examples I–VIII, the liposomes are formed of substantially pure PC. These liposomes act to increase the PC/SM ratio of the heart cells, and to lower cholesterol levels, as will be seen in Example II. The extend of cholesterol reduction can be modulated, from maximum reduction to virtually no reduction, by increasing the amount of cholesterol from zero up to a mole percentage comparable to that in the heart muscle cells of the treated individual.

Another important consideration in the selection of liposome lipids is the acyl chain composition of the phospholipids. As indicated above, the shift from PC to SM phospholipid which occurs with age is also accompanied by an overall increase in the saturation and chain length of the acyl chain moieties of the membrane phospholipids. It is therefore preferred that the PC component of the lipids have an acyl chain composition which is characteristic, at least with respect to transition temperature, of the acyl chain components in heart cells from the animal at a younger age. One preferred PC composition is egg PC, which contains predominantly 1-palmitoyl,2-oleyl PC and 1-palmitoyl,2-linoleyl PC.

The liposomes may contain other lipid components, as long as these are not immunogenic and do not inhibit the desired lipid exchange between the liposomes and heart muscle cells. Additional components may include negatively charged lipids, such as phosphatidylglycerol (PG) or phosphatidylserine (PS). Of course, the mole percentage of these lipids should be relatively low with respect to PC. Lipid protective agents, such as ($\alpha$-tocopherol ($\alpha$-T), $\alpha$-tocopherol acetate, or $\alpha$-tocopherol succinate, may also be included in the lipids forming the liposomes, to protect the lipid components against free radical damage (Levida). Typically such agents are included at a mole percentage between about 0.5% and 2%. It is advantageous to add $\alpha$-T to the liposomes to maintain a balance between vitamin E and polyunsaturated lipids in the liposomes.

A variety of methods for producing liposomes are available, and these have been extensively reviewed (Szoka 1980). In general these methods produce liposomes with heterogeneous sizes from about 0.02 to 10 microns or greater. Since, as will be discussed below, liposomes which are relatively small and well defined in size are preferred for use in the present invention, a second processing step for reducing the size and size heterogeneity of liposomal suspensions will usually be required.

In one preferred method for forming the initial liposome suspension, the vesicle-forming lipids are taken up in a suitable organic solvent system, and dried in vacuo or under an inert gas to form a lipid film in a vessel. An aqueous suspensions medium, such as a sterile saline solution, is added to the film, and the vessel is agitated until the lipids have hydrated to completion, typically within 1–2 hours. The amount of aqueous medium added is such as to produce a final liposome suspension containing preferably between about 10 and 30 g lipid per 100 ml.

The lipids hydrate to form multilamellar vesicles (MLVS) whose sizes range between about 0.5 microns to about 10 microns or larger. In general, the size distribution of MLVs can be shifted toward slightly smaller sizes by hydrating the lipids under more vigorous shaking conditions. Example I describes the preparation of egg PC MLVs, prior to treating the MLVs with ultrasonic irradiation to reduce the liposome sizes.

The aqueous medium used in forming the liposomes may contain water-soluble agent(s) which enhance the stability of the liposomes on storage. A preferred stabilizing agent is an iron-specific trihydroxamine chelating agent, such as desferrioxamine. The combination of a lipophilic free-radical quencher, such as $\alpha$-T, and the water-soluble chelator gave substantially better protection against lipid peroxidation damage than did either protective agents alone. The chelator is included in the aqueous medium in molar excess of the amount of free iron in the medium. Typically, a chelator concentration of between about 10–50 $\mu$M is sufficient.

B. Sizing Liposomes

The liposome suspension may be sized to achieve a selective size distribution of vesicles in a size range less than about 1 micron and preferably less than about 0.2–0.3 microns. Liposomes in this size range can be readily sterilized by filtration through a depth filter. Smaller vesicles also show less tendency to aggregate on storage, thus reducing potentially serious vascular blockage problems when the composition is administered parenterally. Finally, liposomes which have been sized down to the submicron range show more uniform biodistribution and drug clearance characteristics.

Several techniques are available for reducing the sizes and size heterogeneity of liposomes, in a manner suitable for the present invention. Ultrasonic irradiation of a liposome suspension either by bath or probe sonication produces a progressive size reduction down to small unilamellar vesicles (SUVs) between about 0.02 and 0.08 microns in size. A sonicating procedure used to produce SUVs is described in Example I. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane is an effective method of reducing liposome sizes down to a relatively well defined size distribution whose average in the range between about 0.03 and 1 micron, depending on the pore size of the membrane. Typically, the suspension is cycled through the membrane several times until the desired liposome size distribution is achieved. The liposomes may be extruded through successively smaller pore membranes, to achieve a gradual reduction in liposome size.

More recently, it has been discovered that a suspension of liposomes having heterogeneous sizes above and below 1 micron can be sized efficiently by passage through an asymmetric ceramic filter. A preferred ceramic filter is a Ceraflow Microfilter, 0.2–1 $\mu$ inner-surface pore size, available commercially from the Norton Company (Worcester, Mass.), and supplied as a multifilter cartridge-type filter apparatus. This sizing method is described in U.S. patent application for "Liposome Extrusion Method", filed Feb. 13, 1986.

Centrifugation and molecular sieve chromatography are other methods which are available for producing a liposome suspension with particle sizes below a selected threshold less than 1 micron: These two methods both involve preferential removal of larger liposomes, rather than conversion of large particles to smaller ones. Liposome yields are correspondingly reduced.

The size-processed liposome suspension may be readily sterilized by passage through a sterilizing membrane having a particle discrimination size of about 0.2 microns, such as a conventional 0.22 micron depth membrane filter. If desired, the liposome suspension can be lyophilized for storage and reconstituted shortly before use.

II. Treatment Methods and Results
A. Liposome Administration

In one treatment method, the liposomal suspension is administered parenterally in one or more doses until a desired change in the lipid composition of heart muscle cell is produced. Changes in lipid composition in heart muscle cells are accompanied by changes in serum CPK and in red blood cell properties, allowing the course of treatment to be monitored readily by blood sampling.

The liposomes may be conveniently administered as a series of dosages, given over a period of at least several days, and preferably maintained by continued doses at one to several month intervals over the lifetime of the treated individual. The amount of liposomes administered at each dose is preferably between about 0.01 and 1.0 g per kg of body weight and may be substantially less. A typical dose for an 80 kg individual would be between about 40 and 80 grams lipid, corresponding to between 200 and 400 ml of an up to 20% liposome suspension. Administration may be by iv injection, but is preferably done by iv drip over a period of at least about 1 hour, to minimize tissue and blood trauma at the site of administration. The liposomes may be suspended in sterile saline or in a nutritional or drug-containing medium, such as a glucose/salt medium, to combine liposome treatment with other parenteral therapy.

Before the first dose is given, a blood sample is taken for determination of serum enzyme and/or blood cell characteristics which will be monitored during the course of the liposome treatment. As will be discussed below, liposome treatment produces a readily measurable drop in serum CPK level, to a level characteristic of the individual at a much younger age. The fall in CPK presumably reflects a reversal in age-related lipid composition in muscle cells, as documented in Examples II and III, respectively. The liposome treatment is continued until a drop of at least about 25% in serum CPK, and preferably 50% or more, is observed. In the study described in Example II, serum CPK levels declined to about 15% of their pre-treatment values after nine days of treatment.

Liposome treatment also produces easily observable changes in the lipid composition and osmotic fragility of red blood cells. These changes are documented in Examples IV and V below. Osmotic fragility can be determined using simple spectrophotometric techniques to measure percent hemoglobin release when the packed cells are suspended in one of a series narrowly graded salt solutions. The method is described in Example V.

The change in lipid composition of red blood cells can be determined by first extracting blood-cell lipids, then separating selected lipid components by conventional chromatographic methods. PC and SM can be separated readily by thin layer chromatography (TLC) as described in Examples I and IV, for determining the PC/SM ratio. An advantage of following blood cell PC/SM ratio changes to monitor the course of liposome treatment is that relatively large PC/SM changes are observed. For example, in the 9-day treatment described in Example IV, the PC/SM ratio in red blood cells in 18-month old rats increased nearly 7-fold.

Where the therapeutic liposomes are also designed to promote cholesterol exchange from tissues and organs, such as heart tissue cells, to the liposomes (by virtue of low cholesterol content in the liposomes). the course of therapy may also be monitored by following the changes in the cholesterol content. Methods for measuring and expressing changes in membrane cholesterol are detailed in Examples I and III. Changes in phospholipid composition in erythrocytes during liposome treatment are generally more modest than those in PC/SM.

Following the first liposome administration, the levels of serum CPK (or red blood cell characteristic) are measured, and a second liposome dose is given typically 2 and 7 days after the first dose. Further doses may likewise be given at 2–7 day intervals until the serum property being measured begins to plateau. Thereafter, the individual can be maintained at the desired lipid composition state by periodic maintenance. liposome treatments, e.g., every 1–2 months. Example VIII illustrates a treatment regimen in which lab animals were treated initially with two liposome doses spaced a week apart, then maintained with a single liposome injection every two months. The animals showed at least a 36% increase in longevity over untreated animals.

B. Biochemical Effects

The liposome treatment described above was tested in laboratory animals, to determine its effectiveness in reversing age-related changes in the lipid composition of heart muscle cells, and increasing resistance to respiratory stress. In one series of tests, 18 month old rats were treated with three liposome doses, administered every three days for six days (three injections), and the animals were sacrificed three days after the final injection. The PC/SM and cholesterol content of heart muscle cells was determined as detailed in Example II. The values were compared with those obtained from relatively young animals (three months old) and from untreated 18 month old animals. The results show that both the more than twofold decrease in PC/SM ratio and the more than threefold increase in cholesterol content which occur normally between ages three and eighteen months were completely reversed by the liposome treatment.

The three groups of animals were also tested for heart muscle and serum CPK levels, as described in Example III. The changes in lipid composition which normally occur between three and eighteen months in rats is accompanied by approximately threefold increases in both heart muscle cell and serum CPK. After nine days of liposome treatment, heart cell CPK declined about threefold to levels normally seen in 3 month old animals, and serum CPK declined eightfold to a level substantially lower than that in 3 month old animals. The dramatic fall in serum CPK in treated animals thus provides a sensitive indicator of heart lipid changes occurring during liposome treatment. The concomitant reduction in heart muscle CPK during treatment indicates that the fall in serum CPK is in part due to declining levels of heart muscle CPK.

The above-noted changes in heart cell lipid composition were measured on whole heart homogenates, and therefore represent lipid contributions from both myocardial (heart) cells and connective fibroblasts. To confirm that the observed change in lipid composition also reflects changes in myocardial cells, heart cells from three month old and eighteen month old animals were isolated, cultured under conditions which lead to myocardial reaggregates, then tested for lipid exchange with egg PC liposomes. The methods and results are detailed in Example VI. The reaggregates showed a decrease in PC/SM ratio and an increase in cholesterol level, when comparing cells from three and eighteen month old animals, and these age-related changes were substantially reversed by incubation with the egg PC liposomes. The results indicate that the observed lipid effects seen in heart tissue in vivo are due at least in part to changes in myocardial membrane lipids.

Red blood cells from each of the three groups of animals were tested for changes in red blood cell lipid composition and osmotic fragility. The results are discussed above and in Examples IV and V. Briefly, liposome more than reversed age-related changes in PC/SM ratio and cholesterol levels which normally occur between three and eighteen months of age, both increasing the PC/SM ratio and decreasing the cholesterol level with respect to erythrocytes from three month old animals. The change produced in lipid composition is reflected by ability to withstand greater osmotic shock.

III. Therapeutic Uses

A. Increased Resistance to Respiratory Stress

An important therapeutic application of the present invention is increasing an individual's ability to withstand cardiac stress. This application is valuable for individuals who have suffered cardiac trauma, such a myocardial infarction, or who are at high risk of heart trauma. In either case, additional stress on the heart, in the form of increased oxygen demand or elevated blood pressure can cause cardiac failure or serious damage to the heart.

The utility of the treatment has been shown in laboratory animals. Here the animal's ability to withstand cardiac stress before and after treatment was measured by a standard lab procedure, in which an animal is place in a defined-volume chamber which does not allow gas exchange with the outside. During the course of the test, the depletion of oxygen and accumulation of carbon dioxide reduces the animal's blood pressure gradually to near-zero levels. The ability to withstand respiratory stress is measured by the time in the chamber before the animal's blood pressure drops to near zero. The test results are reported in example VII. After three liposome treatments, and nine days after the first treatment, 18 month old male rats were able to maintain blood pressure about 50% longer than untreated rats. The treated rats also showed a much slower rate of increase of serum CPK during the test than untreated animals. Blood monitoring throughout the test period showed that both treated and untreated animals maintained comparable levels of blood oxygen and carbon dioxide, indicating that the better performance of treated animals was not merely a blood-gas content effect.

The inventors and coworkers have previously investigated the relationship between membrane lipid composition and a number of biological properties of rat myocytes in culture, including changes in the level of a number of enzymes, cell morphology, and the beating rate of heart myocytes. The studies, which are mentioned above, showed that the PC/SM ratio of the cells declined severalfold over a fourteen-day culture period and cholesterol content/DNA increased about 1.6-fold in the same period. The addition of PC SUVs to the culture reversed all of the age-related changes in the cell, including membrane lipid composition, enzyme levels, cell morphology, and heart activity, as measured by beat frequency. In particular, the rapid restoration of initial cell beating rate with addition of liposome suggest that lipid composition is a critical factor in heart muscle cell performance, it is likely, therefore, that the increased ability to withstand respiratory shock seen in liposome-treated animals is due, at least in part, to enhanced heart performance.

The treatment procedure generally follows the liposome administration regimen outlined above, in which the individual is given an initial dose of preferably between about 0.5–2 g lipid/kg body weight, and one or more subsequent dose every 2–7 days thereafter, at a long-term dose rate of between about 0.001–1 g lipid/kg animal weight per day. A maintenance dose of between about 0.1–1 g lipid/kg administered every 1–2 months may be employed. The liposome used in the treatment are formulated to promote lipid exchange of PC from the liposomes into the heart cells, and SM exchange in the opposite direction, as described above. The liposomes are also preferably formulated to promote cholesterol exchange from the cells to liposomes, and one preferred liposome formulation is composed of pure egg PC. However, it may be advisable in long-term treatment to include cholesterol in the liposomes, to prevent too much cholesterol depletion in the red blood cells.

Biochemical changes in lipid composition of the heart are monitored, as above, by measuring related changes in serum CPK and/or changes in red blood cell lipid composition or osmotic fragility. Heart functioning can be monitored during the treatment period by conventional EKG.

B. Increased Animal Longevity

According to another aspect of the invention, it has been discovered that laboratory animals which have received liposome treatment, as described above, live significantly longer than untreated animals. The results of a study on longevity of male laboratory rats is described in Example VII. Briefly, 30 month old rats were given an initial injection of liposomes, followed by a second injection 1 week later, and maintenance injections every two months. A group of untreated rats died between ages 32 and 38 months, with an average age of death of about 34 months. The group of treated animals were sacrificed between ages 42 and 48 months.

It is interesting to note that longevity was extended in the treated animals, even though treatment was not begun until a relatively advanced age, i.e., within a few months of the time the animals would normally have died. This finding indicates that liposomes are effective in reversing age-related changes in lipid composition, even at an advanced age. The approximately 36% increase in longevity indicates that the alteration in lipid composition produced by liposome-treatment confers widespread physiological benefits (including, presumably, increased cardiac performance) which are related to longevity. The increase in longevity which is achievable can be appreciated from the projected result in humans. Assuming that a human lives on the average about 2 years for each month of a laboratory rat, liposome treatment would result in a major increase of longevity.

C. Increased Male Sexual Competence

Another benefit conferred by liposome treatment is an apparent increase in fertility of treated males. In the study reported in Example VIII, male lab rats 30 months and older received three liposome doses over a 6 day period. Normally male rats at this age are unable to sire litters when placed in the same cage with younger, otherwise fertile female rats. For example, when ten untreated rats of this age were each housed with three female rats, each 5–6 months old, only two out of the thirty females had litters, and in each case, the litter was smaller than the usual 10–13 animal litter sired by younger males. Treated rats, by contrast, showed normal male fertility. All of the rats sired litters in all three females, and all of the litter sizes were the normal 10–14 size.

The treatment regimen in animals preferably involves a series of liposome injections several days to weeks before mating activity. The course of the treatment can be followed, as above, by monitoring the change in serum CPK or change in erythrocyte properties, as discussed. The treatment is expected to be especially useful in horse and cattle breeding, where extending the breeding life of selected animals would be valuable.

The following examples illustrate various aspects and uses of the present invention, but are in no way intended to limit the scope thereof.

MATERIALS

Egg phosphatidylcholine (egg PC) and bovine brain sphingomyelin (SM) were prepared according to known methods (Shinitsky, Barenholz 1976). Both lipids were more than 99% pure, based on thin layer chromatography analysis. The egg PC fatty acid composition was similar to the reported composition (Hertz). The main PCs of the preparation included 1-palmitoyl,2-oleyl PC and 1-palmitoyl,2-linoleyl PC. Cholesterol, about 99% pure, was obtained from Sigma (St. Louis, Mo.). Thin-layer chromatography plates—0.25 silica gel HR and 0.024 silica gel—were obtained from Merck (Darmstadt, Germany) and Analtech (Newark, Del.), respectively.

EXAMPLE I

Preparation of Small Unilamellar Vesicles

Egg PC dissolved in chloroform was placed in a 100 ml vessel and dried to a thin film under nitrogen. Sterile saline was added to the lipid film to a final concentration of about 100 mg/ml, and the lipid film was hydrated with swirling. The resulting multilamellar vesicle (MLV) suspension was then bath sonicated for 1 hour using a Heat System Sonicator, Model 375W, at a power setting of 40–50% full value. The temperature of the suspension was maintained at about 4° C. under nitrogen during sonication. The sonicated suspension was separated from large vesicles by ultracentrifugation at 100,000 g for 1 hour (Barenholz 1977). The suspension of SUVs, having a concentration of about 100 mg/ml, was filter sterilized.

EXAMPLE II

Effect of Age and SUV Treatment on Lipid Composition in Heart Muscle Cells

The lipid compositions of heart muscle cells in male Wistar rats at age 3 months, 18 months, and 18 months following liposome treatment were examined. Each of the three groups contained six animals, and the animals were injected through the tail vein with either sterile saline (3 month and 18 months untreated groups) or with the SUV suspension of Example 1. The treated animals were injected every three days for six days (a total of three doses) with 0.5 to 1 gm lipid per animal, and the untreated animals received a similar volume of sterile saline over the same period. Three days after the final injection (9 days after the first injection), the animals were sacrificed by exsanguination, and the blood was saved for further analysis.

The heart was removed, washed with cold saline (0.15 M NaCl), and after mincing, either freshly homogenized or frozen at −70° C. for later homogenization. The minced tissue was homogenized in about 10 volumes of cold saline, using a Teflon piston in a glass homogenizer, with about 50 strokes.

A portion of the homogenate was lipid extracted (Folch) and the total phospholipid and cholesterol were determined on the chloroform-rich lower phase, as described previously (Bartlett, Barenholz 1978). The PC and SM content were determined by thin layer chromatography (TLC), by either one-dimensional chromatography on silica gel HR plates, or two-dimensional chromatography on silica gel plates, according to published methods (Yechiel 1985a, Yavin).

The lipid composition data are shown in Table 1 below. The PC/SM ratios are expressed as moles PC per mole SM, and the cholesterol level is expressed as nmoles per $\mu g$ of DNA, which was determined by a standard method (Richards). Total DNA content per volume of homogenate remained relatively constant over time and with liposome treatment. All data represent the average values of six animals.

TABLE I

| Age (months) | SUVs | PC/SM | Chol. |
|---|---|---|---|
| 3 | − | 10 | 100 |
| 18 | − | 4.5 | 333 |
| 18 | + | 13.7 | 80–100 |

The lipid composition data show that PC/SM falls more than twofold and cholesterol increases more than threefold, between ages 3 and 18 months. The age-related changes were completely reversed in 18 months old animals, after nine days of liposome treatment, and in fact the PC/SM was significantly higher than the normal ratio seen at three months.

EXAMPLE III

Effect of Age and SUV Treatment on Heart Cell and Serum CPK

Blood samples from the three groups of animals in Example II (3 months, 18 months, and 18 months treated with SUVS) were centrifuged at low speed to remove blood cells. The resulting serum fractions, and each of the heart cell homogenates prepared in Example II, were assayed for CPK activity. The enzyme was determined using a CPK diagnostic kit obtained from Sigma (St. Louis, Mo.), as described in Sigma Technical Bulletin No. 45-UV. The results are shown in Table II, where heart cell enzyme activity is expressed as mU per $\mu g$ heart cell DNA, and serum enzyme activity, as mU per ml serum.

TABLE II

| Age (months) | SUVs | Heart CPK (mU/$\mu g$ DNA) | Serum CPK (mU/$\mu l$) |
|---|---|---|---|
| 3 | − | 20–25 | 7.5 |
| 18 | − | 65 | 20.0 |
| 18 | + | 20 | 2.5 |

The data show that both heart cell CPK and serum CPK (which represents enzyme which has been released predominantly from muscle tissue) increase two to threefold from ages 3 to 18 months. This increase is completely reversed in heart muscle after 9 days of liposome treatment, and in serum about an 8-fold drop in CPK activity was observed.

EXAMPLE IV

Effect of Age and SUV Treatment on Lipid Composition in Red Blood Cells

The blood cell pellets from Example III were resuspended in cold saline and centrifuged at 1000×g for 5 minutes, and the lymphocyte buffy coat was removed, yielding a fraction of red blood cells. This fraction was washed two times with cold saline to further remove white cells and serum contaminants. The cells were then homogenized gently in cold saline and the red cell membranes fractionated from supernatant by centrifugation at 20,000×g for 20 minutes. A portion of the cell membrane pellet was lipid extracted, and total phospholipids, cholesterol, and PC and SM were determined as described in Example II. Table II below shows PC/SM ratios, expressed as mole PC/mole SM and cholesterol content, expressed as imole cholesterol/μg DNA for the three different animal groups. As in Tables I–II, the data values in Table III represent the averages for six animals.

TABLE III

| Age (months) | SUVs | PC/SM | Chol. |
|---|---|---|---|
| 3 | − | 1.1 | 4.5 |
| 18 | − | 0.6 | 6.0 |
| 18 | + | 4.0 | 3.0 |

As seen, red cells showed about a two fold decline in PC/SM between ages 3 and 18 months, and treatment with PC SUVs at 18 months increased this ratio nearly sevenfold. At the same time, cholesterol showed an approximate 30% rise between ages 3 and 18 months and about a twofold drop after 9 days of liposome treatment.

EXAMPLE V

Effect of Age and SUV Treatment on Osmotic Fragility of Red Blood Cells

The osmotic fragility of the red blood cell samples obtained in Example III was determined according to a standard procedure. Briefly, about 5 μl of washed, packed red blood cells were added to each of ten tubes. The aliquots were pelleted by centrifugation and supernatants removed. To each pellet was added 3 ml of cold saline having a salt concentration ranging from 15 to 150 mM, in increments of 15 mM. The pelleted cells were rapidly resuspended in the added salt solutions by vortexing. After centrifugation to remove intact cells, the supernatant fractions were read spectrophotometrically to determine the amount of released hemoglobin. The percent release was calculated as a fraction of the total amount of hemoglobin released by detergent lysis of the cells. Percent hemolysis at each of the salt concentrations are shown in Table IV.

TABLE IV

| NaCl (mM) | Percent Hemolysis | | |
|---|---|---|---|
| | 3 months | 18 months | 18 months + SUVs |
| 150 | 3 | 7 | 3 |
| 135 | 5 | 7 | 3 |
| 120 | 5 | 7 | 3 |
| 105 | 8 | 18 | 5 |
| 90 | 15 | 73 | 12 |
| 75 | 50 | — | 50 |
| 60 | 100 | — | 75 |
| 45 | — | — | 87 |
| 30 | — | — | 92 |
| 15 | — | — | 94 |

Cells from untreated 3 month old animals showed 50% lysis at about 75 mM and nearly complete lysis at about 60 mM. Cells from untreated 18 month old animals are more osmotically fragile, showing 50% hemolysis at a salt concentration above 90 mM, and complete hemolysis above 75 mM. Cells from liposome-treated 18 months old animals gave about the same osmotic response as cells from young (3 month) animals at salt concentrations between 150–75 mM. At lower salt concentrations, the liposome-treated cells are less osmotically fragile than cells from 3 month old animals, possibly reflecting the higher PC/SM ratio in the treated cells (Table III).

EXAMPLE VI

Effect of Age and SUV Treatment on Heart Cell Reaggregates in Culture

To confirm that the changes in lipid composition of heart cells are in fact occurring in myocardial cells, tie effect of liposome treatment on cultured, reaggregated myocardial cells was also examined. The cultured reaggregates can be formed by digesting minced heart tissue with proteolytic enzymes, such as trypsin or collagenase, until the cells are dissociated, then culturing the cells for a period of a few days until myocardial cell reaggregates are formed (Harary).

In the present study, hearts were obtained from male Wistar rats of each of the following ages: (1) 3 day old neonatal; 3 months; and 18 months. The hearts from each age group were then treated, according to known methods (Jourdon), to yield a suspension of dissociated myocardial cells. Cell reaggregates were formed by placing 10 ml of the cellular suspension (about $5 \times 10^6$ cells/ml) in a 25 ml culture flask, and incubating the cells on a gyratory shaker at 37° C. for 18–24 hours until aggregates formed. The cells were the transferred to Erlenmeyer flasks, and fresh medium was added. For each age group, half of the cell cultures were untreated and half were treated with PC SUVS, prepared as in Example I. Cells were treated with liposomes by adding the SUVs to the second medium, at a final concentration of about 1–5 mM lipid. The cells were cultured for an additional four days, either in the presence or absence of liposomes, at 37° C. in a gyratory shaker. The medium, including liposomes, was changed every 24 hours.

At the end of the six day incubation period, the cells were harvested, washed several times with cold saline, and homogenized into cold saline substantially as described in Example II. A portion of the cell homogenate was lipid extracted, as described in Example II, for determination of cholesterol and PC/SM ratio, and the remainder was examined for CPK activity and DNA content, as described in Example III. The results are shown in Table V below, where CPK is expressed as activity units per μg DNA; cholesterol, as μmole per μg DNA; and PC/SM, as moles PC/mole SM.

TABLE V

| Age | SUV | CPK | Chol. | PC/SM |
|---|---|---|---|---|
| 3D | − | 7 | 0.05 | 2.0 |
| 3M | − | 13 | 0.06 | 1.8 |
| 18M | − | 17 | 0.10 | 0.8 |
| 3D | + | 3 | 0.03 | 2.0 |
| 3M | + | 4 | 0.04 | 2.1 |
| 18M | + | 4 | 0.05 | 2.1 |

The data show the same general lipid composition and CPK trends related to age and liposome treatment as observed with in vivo liposome treatment: CPK activity, which increases with animal age, is markedly reduced by liposome treatment. The approximately twofold increase in cholesterol which occurs between 3 and 18 months was substantially reversed by liposome treatment, as was the approximately twofold decline in PC/SM which occurs between 3 and 18 months.

EXAMPLE VII

Effect of Age and SUV Treatment on Resistance to Respiratory Stress

When an animal is placed in a closed-chamber, the normal atmospheric oxygen in the chamber is gradually replaced with respired carbon dioxide, and the animal is placed under progressive respiratory stress from increased heart beat and breathing rate, elevated blood pH, and falling blood pressure. The length of time which can animal can survive such stress (maintain a positive blood pressure) is one standard method for measuring the animal's resistance to respiratory stress. Not surprisingly, younger animals are generally more stress-hardy in this test.

In the present example, three male Sabra rats, 15–18 months old, were treated with PC SUVs according to the regimen in Example II, i.e., three injections over a six-day period. Three other rats of the same age received equivalent-volume injections of sterile saline. Nine days after the first injection, the animals were tested for respiratory function in a closed 600 ml chamber. The animals were anesthetized and "forced" to breath using a pump pulsing 15 times/min. The animals were monitored during the test period for blood pres-sure (in one limb), electrocardiograms (ECG) and arterial blood samples were taken every five minutes for analysis of blood oxygen and carbon dioxide levels. CPK levels, and pH. The experiment was terminated when the animals' measured blood pressure dropped to zero, and the animal was allowed to breathe normal air.

The average time required for untreated animals to reach a zero blood pressure state was between about 35–45 minutes. Average endurance of treated animals was reached between about 55–65 minutes. Thus, liposome treatment enhanced the ability of the animals to withstand the respiratory stress of oxygen depletion and carbon dioxide accumulation by about 50–60%. Untreated animals maintained a basal level of blood CPK for about 25 minutes, after which enzyme activity increased dramatically until the termination of the test. In treated animals, blood CPK remained substantially unchanged for the first 40–45 minutes, then increased gradually over the remaining test period, at a rate about one-tenth that in the untreated animals.

Blood levels of oxygen, carbon dioxide, and pH, as a function of the duration of the test, were similar in both animal groups, indicating that the increased tolerance to respiratory stress seen in treated animals was not due to different blood levels of oxygen and carbon dioxide.

EXAMPLE VIII

Effect of SUV Treatment on Longevity

This study examines the effect of liposome treatment on animal longevity. The rats tested were 30 month old male Sprague-Dawley rats. Since Sprague-Dawley rats normally die between the ages of about 24–30 months, the rats tested already showed some selection for longevity. A test group of six rats were each given PC SUVS, prepared as in Example I, at a dose of between 0.5 and 1 g liposome lipid through the tail vein, and similarly dosed after one week, and every two months thereafter until the animal died of natural causes. The animals were fed ad libitum during the treatment period and the usual precautions were taken to avoid animal infection. A second control group of same-age male rats was similarly injected with sterile saline on the same dose schedule.

Of the 6 animals in the control group, 2 died at 32 months (two months after the beginning of treatment), 3 died at 34 months, and 1 died at 40 months, giving an average age at death of about 34 months. Of the treated animals, 2 were sacrificed at 44 months, 1 at 45 months, and 3 at 48 months, giving a minimal average age at death of about 46 months.

EXAMPLE IX

Effect of SUV Treatment on Sexual Competence

It is known that sexual function in male rats declines with age. If males 30 months or older are housed with younger, fertile females, many fewer litters, and litter with fewer animals, are born than if the same females had been housed with relatively young rats.

To test the effect of liposome treatment on sexual function, a group of 10 rats, each 34–36 months old, were treated with egg PC SUVs according to the regimen described in Example II. A control group was similarly treated with sterile saline. Nine days after the first injection, the animals were each placed in a cage with 3 female Sprague-Dawley rats 5 to 6 months old. The 1 male and 3 females were housed together for 1,3, or about 7 weeks, after which the males were removed. Only about 1 in 3 females in contact with untreated males for 1 week produced litters, and this rate increased to about 2 of the 3 females after 7 weeks of contact with untreated males. In all cases, litter sizes were less than 10. With treated males, about 2 of the 3 females produced litters with 1 week contact, and virtually all of the females littered with 3 weeks contact. Litter sizes were the normal 10–14 animals.

While various embodiments of the invention have been described herein, it will be apparent that various changes and modifications can be made without departing from the invention.

We claim:

1. A method of reversing age-related changes in heart muscle cells in a subject, comprising intravenously administering to the subject, in a therapeutically effective amount, liposomes having a lipid component comprising phosphatidylcholine having an acyl chain composition which is characteristic, at least with respect to transition temperature, of the acyl chain components of phosphatidylcholines in the heart cells of the subject at a younger age, said liposomes being substantially free of sphingomyelin, and repeating said administering over a period of at least several days until a significant drop in the subject's serum creatinine phosphokinase is observed.

2. The method of claim 1, wherein the phosphatidylcholine is egg phosphatidylcholine.

3. The method of claim 1, wherein the liposomes are unilamellar vesicles in the 0.02 to 0.08 $\mu$m size.

* * * * *

UNITED STATES PATENT AND TRADEMARK OFFICE
CERTIFICATE OF CORRECTION

PATENT NO.    : 6,348,213 B1
DATED         : February 19, 2002
INVENTOR(S)   : Yechezekel Barenholz and Elishalom Yechiel It is certified that error appears in the above-identified patent and that said Letters Patent is hereby corrected as shown below:

<u>Title page</u>,
Item [63], Related U.S. Application Data, change "Pat. No. 4,737,323" to
-- Pat. No. 4,812,314 --.

<u>Column 1</u>,
Line 11, change "4,737,323" to -- 4,812,314 --.

Signed and Sealed this

Thirtieth Day of December, 2003

JAMES E. ROGAN
*Director of the United States Patent and Trademark Office*